(12) United States Patent
Hu et al.

(10) Patent No.: US 10,736,584 B2
(45) Date of Patent: Aug. 11, 2020

(54) MOVABLE PATIENT TABLE

(71) Applicant: GE Precision Healthcare LLC, Wauwatosa, WI (US)

(72) Inventors: Gang Hu, Beijing (CN); Xianfa Fang, Beijing (CN); Yahong Wang, Beijing (CN); Xiaomin Yan, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 103 days.

(21) Appl. No.: 15/964,357

(22) Filed: Apr. 27, 2018

(65) Prior Publication Data
US 2018/0310895 A1 Nov. 1, 2018

(30) Foreign Application Priority Data
Apr. 28, 2017 (CN) .......................... 2017 1 0293882

(51) Int. Cl.
*A61B 6/04* (2006.01)
*A61B 6/10* (2006.01)
*A61B 5/055* (2006.01)
*A61G 13/10* (2006.01)

(52) U.S. Cl.
CPC .......... *A61B 6/0407* (2013.01); *A61B 5/0555* (2013.01); *A61B 6/105* (2013.01); *A61G 13/10* (2013.01); *A61G 13/104* (2013.01)

(58) Field of Classification Search
CPC ..... A61B 5/0555; A61B 6/0407; A61B 6/105; A61G 13/104
See application file for complete search history.

(56) References Cited

U.S. PATENT DOCUMENTS

| 4,439,879 | A | * | 4/1984 | Werner | A61G 7/0528 5/600 |
| 5,348,326 | A | * | 9/1994 | Fullenkamp | A61G 7/00 280/43 |
| 5,377,372 | A | * | 1/1995 | Rudolf | A61G 7/00 16/35 R |
| 5,806,111 | A | * | 9/1998 | Heimbrock | A61G 1/0225 280/47.371 |

(Continued)

*Primary Examiner* — Vishal R Sahni
(74) *Attorney, Agent, or Firm* — Armstrong Teasdale LLP

(57) ABSTRACT

The present invention provides a movable patient table, comprising a table body, a first operating member, a locking member and a transfer member. The first operating member comprises a first operating part. Two ends of the locking member are respectively pivoted to the table body and the first operating member. The transfer member comprises a transfer part and a contact part, the transfer part is pivoted to the first operating member, and a pivoting point pivoted to the table body is provided between the transfer part and the contact part; and in a process that the first operating part is driven to be lowered down from a first released position to a locked position, the locking member and the transfer member respectively rotate around pivoting points with the table body until a pivoting point between the locking member and the table body, a pivoting point between the locking ember and the first operating member and a pivoting point between the transfer part and the first operating member are located on the same straight line, and the contact part rotates to be in contact with a movement plane of the table body.

20 Claims, 2 Drawing Sheets

(56) References Cited

U.S. PATENT DOCUMENTS

| | | | | |
|---|---|---|---|---|
| 6,460,205 B1 * | 10/2002 | Lewandowski | .......... | A61G 7/05 |
| | | | | 5/600 |
| 6,473,921 B2 * | 11/2002 | Brooke | ................. | A61G 7/012 |
| | | | | 16/32 |
| 6,902,019 B2 * | 6/2005 | Heimbrock | ............ | A61G 7/018 |
| | | | | 180/19.1 |
| 7,302,717 B2 * | 12/2007 | Reinke | ................ | B60B 33/0021 |
| | | | | 5/600 |
| 9,173,795 B2 * | 11/2015 | Heidlage | ............. | A61G 7/0528 |

\* cited by examiner

MOVABLE PATIENT TABLE

CROSS-REFERENCE TO RELATED APPLICATIONS

This application claims priority to Chinese Patent Application No. 201710293882.9, filed on Apr. 28, 2017, the entirety of which is incorporated herein by reference.

FIELD OF THE INVENTION

The present invention relates to the medical field, in particular to a movable patient table.

BACKGROUND OF THE INVENTION

In the field of X-ray or magnetic resonance diagnosis and treatment, a patient table is used for carrying a patient such that a doctor can perform medical imaging examination, surgical treatment and the like to the patient at a proper height. Types of patient tables comprise a fixed type and a movable type. Although a movable patient table can be more conveniently moved than a fixed patient table, the stability of the movable patient table is not enough. For example, according to user feedback, after the movable patient table is moved to a target position and is fixed, a probability of shake and even displacement due to external force is still relatively great, and the safety of the patient is possibly influenced thereby.

Therefore, it is necessary to improve the movable patient table such that the movable patient table has stronger stability in addition to the advantage of movability.

BRIEF DESCRIPTION OF THE INVENTION

One purpose of the present invention is to provide an improved movable patient table, which has stronger stability in addition to the advantage of movability.

The exemplary embodiment of the present invention provides a movable patient table, comprising a table body, a first operating member, a locking member and a transfer member. The first operating member comprises a first operating part. Two ends of the locking member are respectively pivoted to the table body and the first operating member. The transfer member comprises a transfer part and a contact part, the transfer part is pivoted to the first operating member, and a pivoting point pivoted to the table body is provided between the transfer part and the contact part; and in a process that the first operating part is driven to be lowered down from a first released position to a locked position, the locking member and the transfer member respectively rotate around pivoting points with the table body until a pivoting point between the locking member and the table body, a pivoting point between the locking member and the first operating member and a pivoting point between the transfer part and the first operating member are located on the same straight line, and the contact part rotates to be in contact with a movement plane of the table body.

Other features and aspects will become clear through detail description, drawings and claims below.

BRIEF DESCRIPTION OF THE DRAWINGS

The exemplary embodiment of the present invention will be descritable with reference to the drawings such that the present invention can be better understood. In the drawings.

DETAILED DESCRIPTION OF THE DRAWINGS

Hereafter, a detailed description will be given for preferred embodiments of the present invention. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art relating to the contents disclosed in the present invention, which should not be regarded as insufficient disclosure of the present invention.

Unless defined otherwise, all the technical or scientific terms used in the Claims and the Description should have the same meanings as commonly understood by one of ordinary skilled in the art to which the present invention belongs. The terms "first," "second" and the like in the Description and the Claims do not mean any sequential order, number or importance, but are only used for distinguishing different components. The terms "a," "an" and the like do not denote a limitation of quantity, but denote the existence of at least one. The terms "comprises," "comprising," "includes," "including" and the like mean that the element or object in front of the "comprises," "comprising," "includes" and "including" cover the elements or objects and their equivalents illustrated following the "comprises," "comprising," "includes" and "including," but do not exclude other elements or objects. The term "coupled" or "connected" or the like is not limited to being connected physically or mechanically, nor limited to being connected directly or indirectly.

Figure 1A:
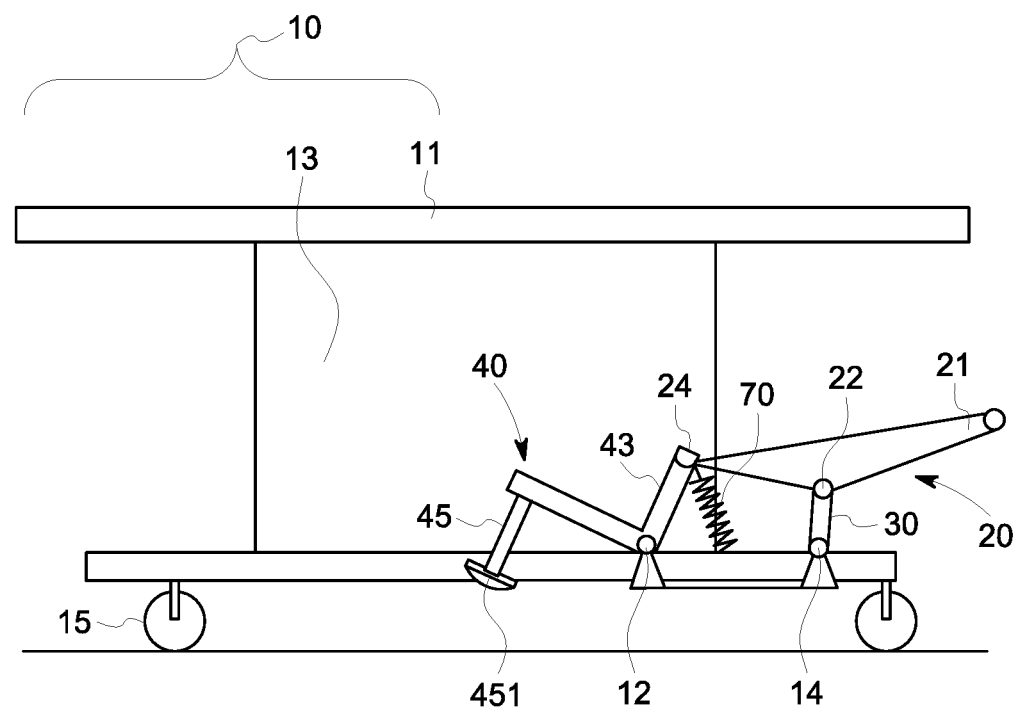
FIGS. 1(a) and 1(b) illustrate structural schematic views of a movable patient table provided by one embodiment of the present invention at a released position and a locked position.
Figure 1B:
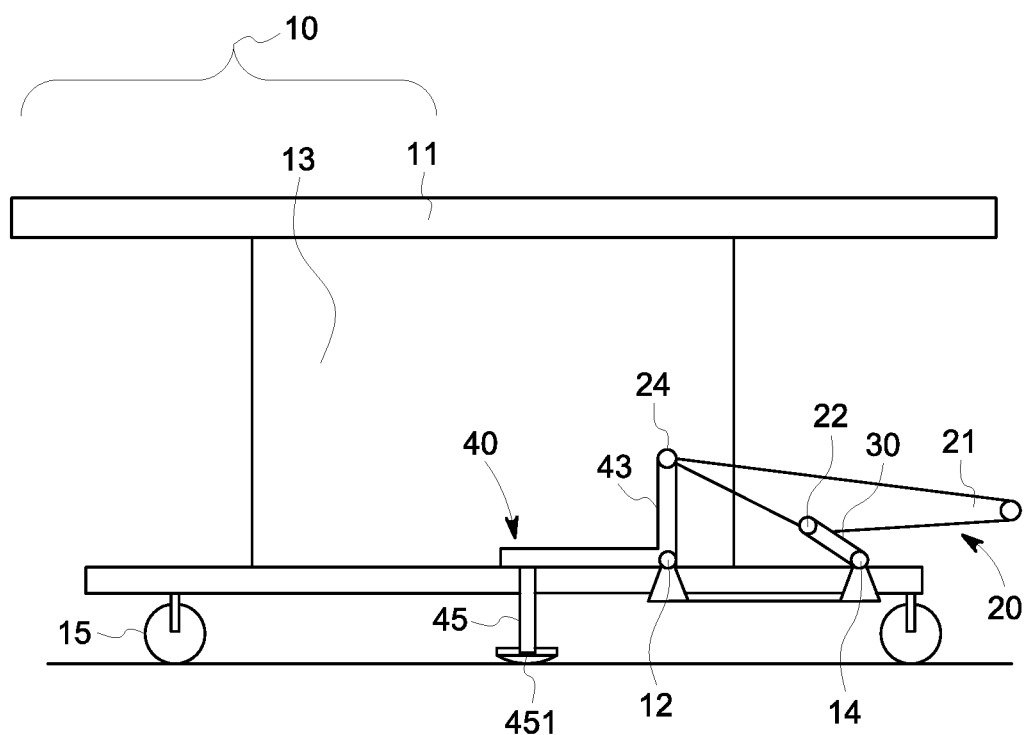

FIGS. 1(a) and 1(b) illustrate structural schematic views of a movable patient table provided by one embodiment of the present invention. Herein, FIG. 1(a) illustrates a schematic view when a first operating part 21 is located at a first released position, and FIG. 1(b) illustrates a schematic view when a first operating part 21 is located a locked position. The movable patient table comprises a table body 10, a first operating member 20, a locking member 30 and a transfer member 40.

One skilled in the art can understood the table body 10 comprises a table 11, a supporting part 13 used for supporting the table 11 and a driving part 15 used for driving the table body to move. The driving part 15 may comprise a rotating part such as a rotating wheel. A control part (not shown) which is used for driving the table 11 to move in a horizontal direction or a vertical direction may be further provided in the supporting part 13.

The locking member 30, the first operating member 20 and the transfer member 40 may be sequentially connected to form a link mechanism, such that the locking member 30 and the transfer member 40 can produce linkage while the first operating member 20 is driven.

The first operating member 20 comprises a first operating part 21. The first operating part may be configured to, for example, stretch out of the table body 10 such that an operator can operate it. Two ends of the locking member 30 are respectively pivoted to the table body 10 and the first operating member 20. The transfer member 40 comprises a transfer part 43 and a contact 45 which are mutually connected, the transfer part 43 is pivoted to the first operating member 20, and a pivoting point 12 pivoted to the table body 10 is provided between the transfer part 43 and the contact part 45.

By operating the first operating part 21, the contact part 45 may be controlled to be in contact with a movement plane of the table body 10, so as to prevent the table body 10 from shaking under an external force. The movement plane may be the ground. Specifically, in a process that the first operating part 21 is driven to be lowered down from a first released position to a locked position, the locking member 30 and the transfer member 40 respectively rotate around pivoting points with the table body 10 until a pivoting point 14 between the locking member 30 and the table body 10, a pivoting point 22 between the locking member 30 and the first operating member 20 and a pivoting point 24 between the transfer part 43 and the first operating member 20 are located on the same straight line, and the contact part 45 rotates to be in contact with the movement plane of the table body 10. When the first operating part 21 is operated such that it is lowered down from the first released position to the locked position, the contact part 45 is in contact with the movement plane of the table body 10, such that the table body is prevented from shaking under a supporting force. At the same time, since the pivoting points 14, 22 and 24 are located on the same straight light, the transfer member 40 is locked at a current position and the transfer member 40 is prevented from rotating, so as to guarantee that the contact part 45 thereof is supported on the movement plane of the table body 10.

Optionally, the first operating part 21 of the first operating member 20 is a pedal. For example, the operator may step on the pedal such that the first operating part 21 is subjected to a downward pressing force to lower down from an initial position (i.e., the first released position) to the locked position.

One skilled in the art should understand that, after the movable patient table is moved to a destination (e.g., an operation room), it may be connected with a fixing device at the destination. The fixing device is used as an external device of the movable patient table, can resist the external force which causes the table body to be displaced, and thereby can prevent the table body fixedly connected thereto from further moving. Therefore, in the current movable patient table, it further comprises a pedal which is used for fixedly connecting the table body 10 to the external device. The first operating part 21 of the first operating member may reuse the pedal. Optionally, the movable patient table in this embodiment may further comprise a first spring 70, one end of the first spring 70 is connected to the table body 10 and the other end is connected to the transfer part 43 of the transfer member 40 to apply a downward pulling force to the transfer part 43. For example, as illustrated in FIG. 1(a), one end, connected to the table body 10, of the first spring 70 may be provided near a bottom portion of the table body 10, such that it is lower than one end, connected to the transfer part 43, of the first spring 70, and the first spring 70 can apply a downward pressing force to the transfer part 43. By adopting this mode, when the movable patient table is in a moving state or other states under which the contact part 45 does not need to be in contact with the movement plane of the table body 10, the transfer member 40 can be prevented from freely rotating and causing the contact part 45 to be in contact with the movement plane of the table body 10 when the first operating part 21 is not operated.

Optionally, the contact part 45 is provided with a friction enhancing member 61 used for enhancing a friction force between the contact part 45 and the movement plane of the table body 10. The friction enhancing member 61 may comprise at least one of a fiber material, a rubber material and a resin material, as long as relative displacement caused by a reason that the friction force between the contact part 45 and the movement plane of the table body is too small can be avoided.

Optionally, as illustrated in FIG. 1(a), connecting lines formed by sequentially connecting the pivoting point 24 between the transfer part 43 and the first operating member 20, the pivoting point 14 between the transfer member 40 and the table body 10 and a center 61 of a contact surface of the contact part 45 with the table body 10 form a triangle, such that the pivoting point 24 between the transfer part 43 and the first operating member 20 and the center 451 of the contact surface of the contact part 45 with the movement plane of the table body 10 have a certain distance along a horizontal direction (e.g., a direction in parallel with the movement plane of the table body 10). Therefore, when the first operating part 21 is located at the locked position, the transfer member 40 has strong stability and can be further prevented from rotating and causing the contact part 45 from being displaced.

Specifically, the transfer member 40 comprises a horizontal part 41, the transfer part 43 is connected with the contact part 45 through the horizontal part 41, the transfer part 43 is formed by vertically upwards extending from the horizontal part 41, the contact part is formed by vertically downwards extending from the horizontal part 41, the horizontal part 41 is pivoted with the table body 10 to form the pivoting point 14, and when the first operating part 21 of the first operating member 20 is located at the locked position, the horizontal part 41 is in parallel with the movement plane of the table body 10. Thereby, when the transfer member 40 is locked, the horizontal part 41 can resist against the horizontal plane of the bottom portion of the table body 10, so as to further enhance the stability and prevent the table body 10 from shaking.

In other embodiments, for the needs such as cost decrease, structural design and the like, the pivoting point 24, the pivoting point 14 and the center 451 of the contact surface of the contact part 45 with the movement plane may also be provided on the same straight line.

Figure 2:
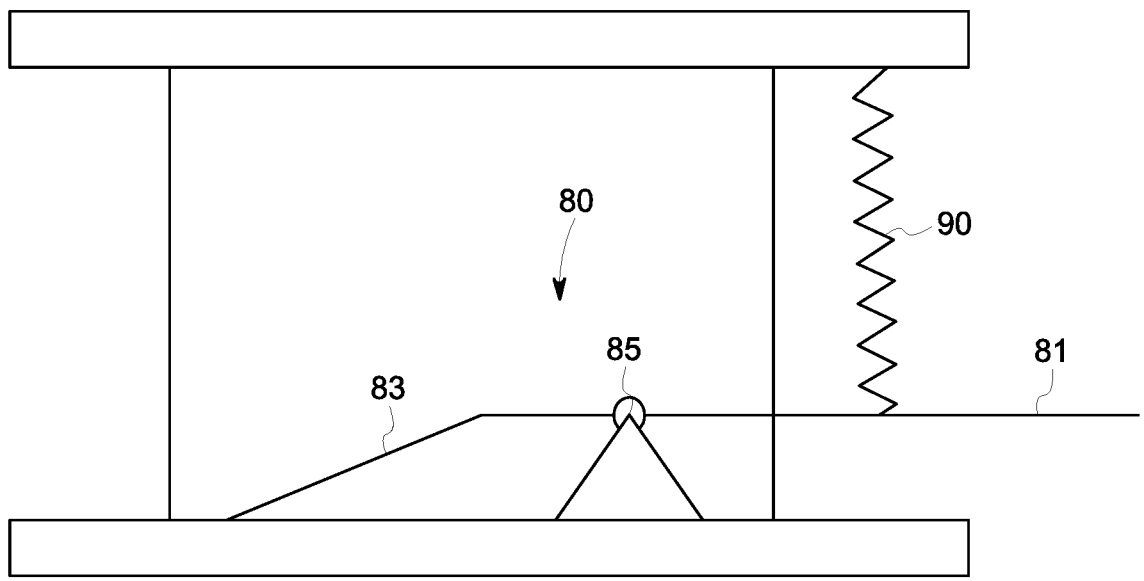
FIG. 2 illustrates a structural schematic view of a movable patient table provided by another embodiment of the present invention.

FIG. 2 illustrates a structural schematic view of a movable patient table provided by another embodiment of the present invention. As illustrated in FIG. 2, the structure and principle of the movable patient table in this embodiment are similar to the structure and principle of the movable patient table in the embodiment illustrated in FIGS. 1(a) and 1(b), and a difference lies in that:

the movable patient table in this embodiment further comprises a second operating member 80 comprising a second operating part 81 and a release part 83, a pivoting point 85 pivoted to the table body 10 is provided between the second operating part 81 and the release part 83, and the release part 83 is located below the first operating member 20 and stretches into a space formed between the first operating member 20 and the transfer member 40. When the second operating part 81 of the second operating member 80 is driven to be lowered down from a second released position, the release part 83 is lifted up and drives the first operating part 21 of the first operating member 20 to be released from the locked position to drive the locking member 30 and the transfer member 40 to respectively rotate around pivoting points with the table body 10 until the contact part 45 is lifted up to leave the movement plane of the table body 10.

The second operating part 81 may be a pedal. Therefore, when the operator needs to fix the table body 10, the first operating part 21 is stepped; and when the table body 10 needs to be released, the second operating part 81 is stepped. The second operating part 81 may be at the same height as the first operating part 21. Since the second operating member 80 is pivoted with the table body 10 at the pivoting point 85, when the second operating part 81 is operated to be lowered down from the second released position, the released part 83 is lifted up under a lever effect and simultaneously drives the first operating member 20 above the release part 83 to be lifted up, such that the first operating member 20 is released from the locked position, the transfer member 40 is driven to rotate and the contact part 45 leaves the movement plane of the table body 10.

Optionally, the movable patient table in this embodiment may further comprise a second spring 90, one end of the second spring 90 is connected to the table body 10 and the other end is connected to the second operating part 81 of the second operating member 80 to apply an upward pulling force to the second operating part 81. Specifically, a connecting position between the first spring 90 and the table body 10 may be provided near a top portion of the table body 10 and be higher than a connecting position between the second spring 90 and the second operating part 81, such that an upward pressing force can be applied to the second operating part 81 and the second operating part is prevented from moving downwards, causing the release part 83 opposite thereto from moving upwards and releasing the contact part 45 when the operator does not operate the second operating part 81.

In other implementation modes, selectively the second operating member may not be provided, and the operator may apply an upward force to the first operating part 21 to enable it to move from the locked position to the first released position, such that the contact part 45 is not in contact with the movement plane of the table body any longer.

In the movable patient table provided by the embodiment of the present invention, by respectively pivoting the locking member and the transfer member to the table body and pivoting the first operating member with the locking member and the transfer member, the transfer member can be fixed when the first operating part of the first operating member is moved to the locked position, further the contact part of the transfer member is in contact with the ground, the table body is fixed by using the friction force between the contact part and the ground and the table body is prevented from shaking under the effect of external force. In addition, the first operating member can also return to the first released position from the locked position, such that the contact part 45 is controlled to leave the movement plane of the table body 10 when the table body 10 needs to be moved. Therefore, the movable patient table in this embodiment has stronger stability in addition to the advantage of movability, the safety of the patient can be guaranteed, and the diagnosis and treatment carried out by the patient to the patient are facilitated.

Some exemplary embodiments have already been described above. Of course, it should be understood that various modifications may be made. For example, if the described technique is executed in difference sequences and/or if the components in the described system, structure, device or circuit are combined in different ways and/or are substituted or replenished by other components or equivalents thereof, proper results can be realized. Correspondingly, other implementation modes also fall into the protection scope of the claims.

The present invention provides a movable patient table, comprising a table body, a first operating member, a locking member and a transfer member. The first operating member comprises a first operating part. Two ends of the locking member are respectively pivoted to the table body and the first operating member. The transfer member comprises a transfer part and a contact part, the transfer part is pivoted to the first operating member, and a pivoting point pivoted to the table body is provided between the transfer part and the contact part; and in a process that the first operating part is driven to be lowered down from a first released position to a locked position, the locking member and the transfer member respectively rotate around pivoting points with the table body until a pivoting point between the locking member and the table body, a pivoting point between the locking member and the first operating member and a pivoting point between the transfer part and the first operating member are located on the same straight line, and the contact part rotates to be in contact with a movement plane of the table body.

What is claimed is:

1. A movable patient table, comprising:
  a table body configured to move relative to a surface;
  a first operating member comprising a first operating part movable between a released position and a locked position;
  a locking member having a first end pivotably connected to the table body at a pivot point and a second end pivotably connected to the first operating member at a pivot point;
  a transfer member comprising a transfer part, a contact part, and a connection part between the transfer part and the contact part, the transfer part pivotably connected to the first operating member at a pivot point, the connection part pivotably connected to the table body at a pivot point, the transfer part extends from the connection part in a first direction, the contact part extends from the connection part in a second direction opposite the first direction, and wherein the connection part is substantially parallel to the surface when the first operating part of the first operating member is in the locked position; and
  a spring connected to the table body and the transfer part of the transfer member, the spring configured to bias the contact part of the transfer member away from the surface when the first operating part is in the released position,
  wherein the pivot point between the locking member and the table body, the pivot point between the locking member and the first operating member and the pivot point between the transfer part and the first operating member are located on a straight line when the first operating member is in the locked position, and
  wherein the contact part of the transfer member is spaced from the surface when the first operating part is in the released position and the contact part is in contact with the surface when the first operating part is in the locked position.

2. The movable patient table according to claim 1, wherein the first operating part of the first operating member is a pedal.

3. The movable patient table according to claim 1, wherein the movable patient table further comprises a pedal used for fixedly connecting the table body to an external device, the first operating part of the first operating member is moved by the pedal.

4. The movable patient table according to claim 1, wherein one end of the spring is connected to the table body and the other end is connected to the transfer part of the transfer member at the pivot point between the transfer part and the first operating member.

5. The movable patient table according to claim 1, wherein the movable patient table further comprises a second operating member comprising:
   a second operating part;
   a release part; and
   a pivoting point between the second operating part and the release part, the pivoting point movably connected to the table body, the release part is located between the first operating member and the transfer member and is movable between a first position and a second position, wherein movement of the release part from the first position to the second position causes the first operating part of the first operating member to move from the locked position to the released position.

6. The movable patient table according to claim 5, wherein the movable patient table further comprises a second spring, one end of the second spring is connected to the table body and the other end is connected to the second operating part of the second operating member.

7. The movable patient table according to claim 1, wherein the contact part is provided with a friction member to provide a friction force between the contact part and the surface.

8. The movable patient table according to claim 7, wherein the friction member comprises at least one of a fiber material, a rubber material and a resin material.

9. The movable patient table according to claim 1, wherein the pivoting point between the transfer part and the first operating member, a pivoting point between the transfer member and the table body and a center of a contact surface of the contact part with the table body form a triangle.

10. The movable patient table according to claim 1, wherein the table body is fixed by a friction force between the contact part and the surface when the contact part is in contact with the surface.

11. The movable patient table according to claim 10, wherein the movable patient table further comprises a driving part for moving the table body relative to the surface.

12. The movable patient table according to claim 1, wherein the first operating member is a triangle including a first corner, a second corner, and a third corner, the first operating part disposed at the first corner of the first operating member, the second end of the locking member pivotably connected to the second corner of the first operating member, the transfer part of the transfer member pivotably connected to the third corner of the first operating member, wherein one end of the spring is connected to the table body between the locking member and the transfer member, and the other end of the spring is connected to the pivot point between the transfer part and the first operating member.

13. A locking apparatus for a movable patient table, the locking apparatus comprising:
   an operating member movable between a released position and a locked position;
   a locking member having a first end and a second end, the first end movably connected to the operating member at a first pivot point, the second end movably connected to a table body of the movable patient table at a second pivot point; and
   a transfer member including:
      a connection part configured to extend substantially parallel to a surface when the operating member is in the locked position;
      a transfer part extending from the connection part in a first direction, wherein the transfer part is movably connected to the operating member at a third pivot point, wherein the first pivot point, the second pivot point, and the third pivot point are located on a line when the operating member is in the locked position; and
      a contact part extending from the connection part in a second direction opposite the first direction, the contact part configured to contact the surface when the operating member is in the locked position; and
   a spring connected to the transfer member to bias the contact part away from the surface when the operating member is in the released position.

14. The locking apparatus according to claim 13, wherein one end of the spring is connected to the transfer member at the third pivot point.

15. The locking apparatus according to claim 13, wherein the operating member comprises a pedal.

16. The locking apparatus according to claim 13, wherein the operating member is a first operating member, the locking apparatus further comprising a second operating member comprising a second operating part, a release part, and a pivoting point between the second operating part and the release part, the pivoting point movably connected to the table body, the release part is located between the first operating member and the transfer member and is movable between a first position and a second position, wherein movement of the release part from the first position to the second position causes the first operating member to move from the locked position to the released position.

17. The locking apparatus according to claim 16, wherein one end of the spring is connected to the table body and the other end is connected to the second operating part of the second operating member.

18. The locking apparatus according to claim 13, wherein the contact part is provided with a friction member to provide a friction force between the contact part and the surface.

19. The locking apparatus according to claim 18, wherein the friction member comprises at least one of a fiber material, a rubber material and a resin material.

20. The locking apparatus according to claim 13, wherein the third pivot point, a pivoting point between the transfer member and the table body and a center of a contact surface of the contact part with the table body form a triangle.

* * * * *